United States Patent [19]

Kissel

[11] Patent Number: 4,695,362
[45] Date of Patent: Sep. 22, 1987

[54] ACID OR ACID SALT WASH OF A METAL CHLORIDE LAYER OF AN ION SELECTIVE ELECTRODE

[75] Inventor: Thomas R. Kissel, Rochester, N.Y.

[73] Assignee: Eastman Kodak Company, Rochester, N.Y.

[21] Appl. No.: 911,560

[22] Filed: Sep. 25, 1986

Related U.S. Application Data

[63] Continuation-in-part of Ser. No. 813,162, Dec. 24, 1985, abandoned.

[51] Int. Cl.$^4$ ............................................. G01N 27/46
[52] U.S. Cl. ..................................... 204/419; 204/418; 204/435; 427/126.1; 427/343
[58] Field of Search ................................. 204/416–420, 204/435; 427/126.1, 343

[56] References Cited

U.S. PATENT DOCUMENTS

| | | | |
|---|---|---|---|
| 3,111,478 | 11/1963 | Watanabe | 204/435 |
| 3,617,101 | 11/1971 | Anderson | 204/435 |
| 3,856,649 | 12/1974 | Genshaw et al. | 204/435 |
| 4,031,606 | 6/1977 | Szonntagh | 204/435 |
| 4,199,411 | 4/1980 | Kim | 204/1 |
| 4,214,968 | 7/1980 | Battaglia et al. | 204/195 |

OTHER PUBLICATIONS

Clin. Chem., vol. 30, pp. 1113–1114 (1984).
Annals. of Clinical Chemistry & Laboratory Science, vol. 10, pp. 523–528 (1980).
J. of Photog. Sci., vol. 28, pp. 121–127 (1980) & vol. 30, pp. 208–215 (1982).
Analytical Chem., vol. 53, pp. 1164–1170 (1981).

*Primary Examiner*—T. Tung
*Attorney, Agent, or Firm*—Dana M. Schmidt

[57] ABSTRACT

There are disclosed a process and the product produced by the process, of making an ion selective electrode for chloride. The process features, after forming a metal chloride layer, the step of washing the electrode in an organic acid, inorganic acid, or a solution of a salt of the acids having certain specified properties.

6 Claims, No Drawings

4,695,362

ACID OR ACID SALT WASH OF A METAL CHLORIDE LAYER OF AN ION SELECTIVE ELECTRODE

This application is a continuation-in-part application of U.S. Ser. No. 813,162 filed on Dec. 24, 1985, now abandoned.

FIELD OF THE INVENTION

This invention relates to a process, and its product, of forming an ion selective electrode. It more particularly concerns the formation of the chloride electrode.

BACKGROUND OF THE INVENTION

Ion selective electrodes, hereinafter ISE's, have become a significant part of the clinical chemists' arsenal in analyzing for analytes in biological fluids. Such ISE's allow for the activity determination of ionic analytes such as $Cl^\ominus$, $Na^\oplus$, $K^\oplus$ and $HCO_3^\ominus$. These ionic analytes are useful in diagnosing, e.g., various acidosis conditions, and in the case of $Cl^\ominus$, adrenal disease and renal failure.

For the $Cl^\ominus$ ISE, useful electrode constructions and preparations are described in U.S. Pat. Nos. 4,214,968, issued July 29, 1980, and 4,199,411, issued Apr. 22, 1980. Such $Cl^\ominus$ ISE is preferably prepared by forming a layer of silver on a suitable support, and thereafter converting a surface portion of the silver layer to silver chloride by treating the silver layer with a chlorochromate bath or wash. Useful examples of such a bath or wash are described in the aforesaid patents.

The most preferred construction of the $Cl^\ominus$ ISE is one in which a thin overlayer, preferably of a cellulose ester, is formed on the silver chloride layer, as described in the aforesaid '411 patent. Although such an overlayer is not essential, it is useful in those occasional instances in which there is a potential for significant uric acid interference in the biological liquid being analyzed. That is, such overlayer has been found to be effective in reducing such interference (as well as interference from e.g., bromide ions). Uric acid, as is well known, is an endogenous purine that can be found as a natural metabolite in human body liquids.

Although such an overcoated $Cl^\ominus$ ISE has been found to be very effective and useful, there have been a few instances in which the ISE was found to produce a large negative bias, representing a falsely reduced $Cl^\ominus$ concentration, when used with test samples containing purines other than uric acid, e.g., hypoxanthine, allopurinol, caffeine, adenine, xanthine, theophylline and the like. These results are reported in, e.g., Clin. Chem., Vol. 30, p. 1113–1114 (1984). Such purines can occur in the patient sample from, e.g., treatment for cancer such as leukemia, when there is also acute renal failure.

Thus, prior to this invention the problem has been to provide a way of reducing the bias in the $Cl^\ominus$ ISE that can be caused by purines other than uric acid. This has not been a facile problem to resolve, for the following reasons:

One approach was to form the AgCl layer by an alternative method different from the chlorochromate wash noted above. In such cases, the purines noted above do not create the bias problem. However, this solution is not particularly desirable, because the use of chlorochromate oxidizing agents appears to be more effective than the noted alternatives, in reducing interference from bromide ions.

Another approach that was considered was a decrease in the permeability of the cellulose ester overcoat so as to hinder the other purines, as well as uric acid, from reaching the AgCl surface. However, this is unsatisfactory because such a decreased permeability renders the ISE less able to be operative within the desired read time, e.g., about three minutes.

For the noted reasons, the purine bias problem caused by the purines other than uric acid remained to be solved by the instant invention.

SUMMARY OF THE INVENTION

This invention is based on the discovery that a step of washing the surface of the silver chloride layer in an appropriate acid is effective, by an unknown surface phenomenon, to reduce the negative bias caused by the presence of purines.

More specifically, in accord with one aspect of the invention there is provided a process for making an ion selective electrode selective for chloride, comprising the steps of (a) forming a layer of silver on a support, and (b) oxidizing a surface portion of the silver layer with a bath comprising a chlorochromate, to form silver chloride. This process is improved in that, after step (b) a further step is included of washing the electrode in an organic acid, inorganic acid, or salt of the organic or inorganic acid, provided that (a) the acid has a pKa < 4.0 and a silver solubility product $pK_{sp}$ < 10.0, in a concentration and for a length of time effective to reduce negative biases created by purine interferences when using an electrode prepared without the further step; and (b) the salt:
(i) is soluble in water at $\geq 0.001M$,
(ii) yields an aqueous pH of $\leq 7.0$, and
(iii) comprises ions that do not dissolve the silver chloride, the cations being univalent or divalent cations only.

In accord with another aspect of the invention, there is provided an ion selective electrode selective for chloride, comprising a support, a layer of silver on the support, and a layer of silver chloride on the silver layer. The electrode is improved in that the silver chloride layer has a surface prepared by washing said electrode in an organic or inorganic acid having a pKa and $pK_{sp}$, and at a concentration and for a length of time, noted above, or in a solution of a salt of an organic or inorganic acid, provided that the salt has the features noted above in the previous paragraph.

As used herein, the purine negative biases noted above are deemed to be "reduced" if there is at least a 10% reduction in the negative bias that occurs for an identical electrode prepared without using the invention, and when testing with a purine interference that creates a negative bias in the absence of the invention. Thus, "purine interference" means, from a purine that actually alters the expected reading in the absence of the invention (which is not the case for just uric acid when using an ISE having a cellulose acetate overcoat.)

Thus, it is an advantageous feature of the invention that a $Cl^\ominus$ ISE is provided with a reduced or no negative bias in the presence of purines, compared to what would be the case without using the invention.

It is a related advantageous feature of the invention that such an ISE is provided without sacrificing its ability to avoid biases created by bromide interference.

It is another related, advantageous feature of the invention that such an ISE is provided from which ion activity values can be read after 3 minutes of contact with a biological liquid.

DESCRIPTION OF THE PREFERRED EMBODIMENTS

The present invention is particularly described with reference to a preferred $Cl^{\ominus}$ ISE prepared with a cellulose ester overcoat on a silver chloride layer formed on a silver conductive metal layer. In addition, it is also useful in reducing negative purine biases for such $Cl^{\ominus}$ ISE's lacking such overcoats, and regardless of the conductive metal selected. That is, the process can be applied to a layer of MCl, where M is a conductive metal such as Ag, Ni, Cu and Au. If no cellulose ester overcoat is present, then the wash step is effective even against uric acid as the purine.

As used herein, "negative bias" refers to an increased positive ISE potential that represents an increase in $Ag^{\oplus}$ activity. The net effect is to predict a lower $Cl^{\ominus}$ concentration than is actually the case.

The conventional steps of preparing the $Cl^{\ominus}$ ISE are, as noted above, described in the aforesaid two U.S. patents. For the reasons noted, the preferred oxidizing step to form the AgCl employs a chlorochromate bath at a temperature of $23° \pm 2°$ C. Such a bath can comprise a chlorochromate of any cation, e.g., $Na^{\oplus}$ or $K^{\oplus}$. The preferred bath features the $K^{\oplus}$ form, in a concentration of from about 0.002M to about 0.2M. The most preferred composition of such a bath comprises 0.15M HCl, 0.2M KCl, and 0.034M $K_2Cr_2O_7$. In the most preferred use of this bath, the silver layer passes through the bath at 3–9 m/minute to convert about 25–40 weight % of the silver to silver chloride, at the surface.

An optional, but preferred, final step is the overcoating of the silver halide layer with the layer (cellulose ester, e.g., cellulose acetate, noted above). Such an overcoat and its preparation are amply described in the aforesaid '411 patent. It is because of such overlayer that the reduction in negative bias achieved by the invention is apparent for purines other than uric acid. That is, the overcoat itself is significantly effective in preventing a bias due to uric acid. Of course, if the overcoat is omitted, then the invention will demonstrate a reduction in negative bias, compared to an untreated ISE, even for uric acid interference.

In accord with the invention, the silver halide layer of the electrode is treated with a selected inorganic or organic acid, or a salt thereof having certain required properties, in a concentration and for a time effective to reduce the negative bias. The acids that are useful for this purpose have a pKa of less than 4.0, and do not dissolve silver chloride, that is, have a silver solubility product less than 10.0, e.g., nitric acid, sulfuric acid, phosphoric acid, hydrochloric acid, formic acid, lactic acid and the like, as well as mixtures of these. If the pKa is >4.0, then the acid is too weak to have an effect. If the $pK_{sp}$ is >10.0, then it will dissolve silver chloride, which is unacceptable. Of these acids, the most preferred are those having a silver complexation constant $K_c < 100$, e.g., nitric acid and phosphoric acid.

It has also been found that certain acid salts are useful as an alternative to the above-noted acids, namely those in which the salt:

(i) is soluble in water at $\geq 0.001M$,
(ii) yields an aqueous pH of $\leq 7.0$, and
(iii) comprises ions that do not dissolve the silver chloride, the cations being univalent or divalent cations only.

Salts that fail to provide these conditions are unsatisfactory; thus not all acid salts can be used. (For example, mercuric salts and salts of $Br^{\ominus}$ and $I^{\ominus}$ tend to dissolve the AgCl.) A solution of the following salts is highly preferred: $NaNO_3$, $Ca(NO_3)_2$, $CdSO_4$ or $FeSO_4$ at a concentration of at least 0.015M, for a length of time of between about 0.5 min and about 5 min.

It has been found that the order in which the silver chloride layer is treated with this acid or salt is not particularly critical. That is, the treatment can occur either immediately after the oxidation step used to convert the surface of the silver layer to silver chloride, e.g., while, it is still wet. Alternatively, the electrode so converted can be dried, aged, and thereafter treated. In any event, the treatment comes before the electrode is overcoated, if at all, with the cellulose ester overcoat described above. It may, of course, be necessary to adjust treatment conditions to ensure that the AgCl layer is not significantly dissolved during the treatment. Furthermore, AgCl layers that have been dried and aged (but not yet overcoated) require and also tolerate a greater acid strength, for a given residence time, to produce the same reduction in purine negative bias as is achieved when the AgCl layer is treated fresh and wet, out of the oxidizing bath.

Thus, as will be readily apparent, the concentration of the acid or salt as well as the time of residence of the electrode within the acid or salt will vary. Selection of the appropriate values depend primarily upon a) the acid or salt selected and b) whether the treatment is to a fresh AgCl surface, or one that is aged. Selection of an appropriate concentration and residence time within these guidelines is well within the skill of the skilled artisan. By way of example, for treatment with nitric acid, using an electrode having a dried and aged silver chloride layer, the concentration of the acid or salt can be between 0.001M and 1.0M, for a residence time of between about 2000 sec and about 30 sec, respectively. Preferably the concentration is between about 0.01M and about 1.0M for a residence time of the electrode that is between about 300 sec and about 30 sec, respectively. Most preferably, the concentration is no less than about 0.05M with a residence time no greater than about 120 sec.

However, the residence time is preferably much shorter than these figures, or the $HNO_3$ concentration considerably weaker, if the treatment is applied to a wet, freshly formed AgCl layer.

The selection of concentration and residence time will also depend upon the purine interference that is contemplated. That is, if the acid or salt concentration is selected to ensure, e.g., a 10% reduction in observed purine bias, the necessary concentration of acid or salt for a given residence time varies somewhat, depending on the identity of the purine and its test concentration, used for the test. For the purpose of the examples hereinafter described, the purine selected was hypoxanthine at 2 mM.

The following is a simplified test to determine whether a particular acid or salt is useful in this invention: The electrode with its metal chloride layer already formed, and aged at least 1 month, is washed with the candidate acid at the selected strength and for the selected time. An identical electrode having metal chloride of the same age is washed with water as a control, for the same time period. The two electrodes are then checked in the following cell: ⊕Orion F ISE/100 μl of sample/M/MCl⊖, where M is the metal of the electrode, and the sample liquid comprises 115 mM NaCl, 25 mM NaHCO$_3$, 10 mM KF in H$_2$O, and 2 mM hypoxanthine. (All mM amounts are expressed per liter, as is conventional.) The cell is read between 1 and 20 sec after spotting, the same read time being made on the control electrode. If at least a 10% reduction is found in the negative bias, compared to the control electrode washed only with water, then the acid or salt, its strength, and its wash time are appropriate.

The selection of a variety of acids or salts for the treatment can also require additional steps. For example, if HCl is used, it is preferred that an H$_2$O wash step be used thereafter, which may not be needed for the other acids. The reason of course is to remove Cl⊖ ions from the AgCl surface and thus to avoid an artificially high Cl⊖ blank being sensed by the reference liquid on the reference side of the differential measurement.

EXAMPLES

The following examples further illustrate the scope of the invention.

In the following examples, except where otherwise stated, the test cell was the following: ⊕Orion F ISE/100 μl of sample/Ag/AgCl⊖. The control fluid comprised 115 mM NaCl, 25 mM NaHCO$_3$, and 10 mM KF in H$_2$O. The purine fluid was the control fluid plus 2 mM hypoxanthine (purine) dissolved therein. The difference in potentials ΔmV, wherein $$\Delta mV = V_{purine\ fluid} - V_{control\ fluid}$$

was measured at the time stated, after metering. It will be appreciated, however, that such attempts to make a single point reading in time are only rough estimates of what is essentially a non-equilibrium condition. Therefore, the same read time was used within a given set of experiments.

Because this test cell is of opposite polarity than in the case of the commercial analyzer test, the sign of the ΔmV data in Tables I and II has been reversed to be consistent with the commercial case in Table III (+ΔmV≃-percent Cl⊖ bias). In both instances, the purine compounds caused a negative bias on chloride ISE's.

EXAMPLES 1-7

Various Acids

In each example, the AgCl layer of the ISE's was prepared using the above-described potassium chlorochromate bleach, and thereafter dried. After some aging, which varied from example to example, the electrode was dipped into a bath of the stated acid for the stated time. (The control in each example was selected to be exactly the same age as the examples against which it was compared, and was washed only in water.) After the treatment time, they were blotted with filter paper and oven-dried at 50° C. for 5 minutes. No cellulose acetate overcoat was applied. The test in the cell described above was then run, after the time indicated to determine whether the acid treatment produced at least a 20% reduction in the positive ΔmV value noted for the control. The results appear in Table I.

TABLE I

| Example | Acid Composition of Bath | Residence Time in Bath (sec) | Read Time After Spotting (sec) | ΔmV | % Reduction Against Control ΔmV |
|---|---|---|---|---|---|
| Control | None | None | 5 | 2.7 | — |
| 1 | 0.005 M HNO$_3$ | 300 | 5 | −3.0 | ≃200 |
| Control | None | None | 10 | 8.15* | — |
| 2 | 0.15 M HNO$_3$ | 30 | 10 | −6.1 | 175 |
| 3 | 0.05 M H$_3$PO$_4$ | 30 | 10 | −9.5 | 217 |
| 4 | 0.15 M HCl | 30** | 10 | 1.3 | 84 |
| 5 | 0.15 M formic acid | 30 | 10 | −2.3 | 128 |
| Comp. Ex. 1 | H$_2$O with no acid | 30 | 10 | 14.3 | No reduction |
| Control | None | None | 5 | 6.5 | — |
| 6 | 0.025 M H$_2$SO$_4$ | 300 | 5 | 2.2 | 66 |
| Control | None | None | 3 | 3.5 | — |
| 7 | 0.15 M lactic acid | 30 | 3 | −3.1 | ≃200 |
| Comp. Ex. 2 | H$_2$O only | 30 | 3 | 4.1 | No reduction |

*An average of two readings.
**Followed by a 30 sec H$_2$O rinse.

EXAMPLES 8-15

Variations in Concentration and Residence Time

Example 1 was repeated, but for these examples, the concentrations and residence times were those listed in Table II.

TABLE II

| Example | Acid Composition of Bath | Residence Time in Bath (sec) | Read Time After Spotting (sec) | ΔmV | % Reduction Against Control ΔmV |
|---|---|---|---|---|---|
| Control | None | None | 30 | 21.8 | — |
| 8 | 0.1 M HNO$_3$ | 120 | 30 | 12 | 41 |
| 9 | 0.1 M HNO$_3$ | 60 | 30 | 8 | 63 |
| 10 | 1.0 M HNO$_3$ | 30 | 30 | 12 | 41 |
| Control | None | None | 30 | 17.5 | — |
| 11 | 0.01 M HNO$_3$ | 1800 | 30 | 3.0 | 77 |
| Comp. Ex. 3 | 0.01 M HNO$_3$ | 120 | 30 | 19.2 | No reduction |

TABLE II-continued

| Example | Acid Composition of Bath | Residence Time in Bath (sec) | Read Time After Spotting (sec) | ΔmV | % Reduction Against Control ΔmV |
| --- | --- | --- | --- | --- | --- |
| Control | None | None | 5 | 2.7 | — |
| 12 | 0.05 $\underline{M}$ HNO$_3$ | 300 | 5 | −3.0 | ≃200 |
| 13 | 0.01 $\underline{M}$ HNO$_3$ | 1800 | 5 | −4.6 | 270 |
| Control | None | None | 3 | 2.2 | — |
| 14 | 0.05 $\underline{M}$ HNO$_3$ | 30 | 3 | 1.7 | 23 |
| 15 | 0.1 $\underline{M}$ HNO$_3$ | 30 | 3 | 0.9 | 59 |
| Comp. Ex. 4 | 0.2 $\underline{M}$ HNO$_3$ | 30 | 3 | 5.3 | No reduction |

The two Comparative Examples 3 and 4 were unsuccessful because of an improper combination of acid concentration and residence time. In the case of Comparative Example 3, the residence time was insufficient, whereas it was too long for Comparative Example 4. It is believed in the latter case that there was detrimental removal of the AgCl layer and possibly of the Ag layer.

Conversely, the strength of the acid in Example 10 was not too strong, even though greater in absolute value than the strength of the acid in Comparative Example 4. The reason was that the electrode in Example 10 was much older than the one in Comparative Example 4 (greater than 24 months versus less than 3 months, respectively). The greater aging made Example 10 more tolerant of the greater acid strength.

EXAMPLES 16-17

Results When Overcoated with Cellulose Acetate

The procedure of Example 1 was repeated, except as follows:

The acid wash was applied to a freshly prepared AgCl layer while the latter was still wet, using the same process line as for the bleach bath. After the treatment in the acid noted in Table III, an overcoat of cellulose acetate of a thickness of 10-20 μm was prepared as described in the aforesaid U.S. Pat. No. 4,199,411. The testing of the electrodes was done using a human serum pool spiked with 0.455 mM hypoxanthine. The control was the same, but without the hypoxanthine. The measuring cell was the "Ektachem Cl$^\ominus$" TM test elements prepared using the noted ISE's, read on the "Ektachem 400" TM analyzer manufactured by Eastman Kodak Co., with electrometer readings being taken after 3 minutes. The "Ektachem" reference fluid was used on the reference side of the test. All electrometer readings were converted to Cl$^\ominus$ concentrations via previously measured calibration lines.

TABLE III

| Example | Acid Composition of Bath | Residence Time in Bath (sec) | Read Time After Spotting (min) | % [Cl]* Bias | % Reduction Against Control |
| --- | --- | --- | --- | --- | --- |
| Control | None | None | 3 | −9.87 | — |
| 16 | 0.015 $\underline{M}$ HNO$_3$ | ≃30 | 3 | −1.1 | ≃85 |
| 17 | 0.015 $\underline{M}$ H$_3$PO$_4$ | ≃30 | 3 | +1.32 | ≃113 |

*% [Cl] bias = 100([Cl] purine - [Cl] control fluid)/[Cl] control fluid. Replicate precision on any given [Cl] prediction is about ± 0.7%.

EXAMPLES 18-21

Various Salts

The procedure of Example 16 was repeated, except salts of acids were used to prepare the wash solution, instead of acids. The wash time was the same for the control (no acid salts present, just deionized water) and the salt solutions, namely 3 min. The test fluids and the control fluids were the same as for Ex. 16. The tests were run after an aging period of 1 month, while stored at the temperature indicated in Table IV.

The sodium acetate, comparative ex. #5, was selected because it has an aqueous pH above 7.0. It was unsatisfactory, as shown in Table IV:

TABLE IV

| Example | Salt Composition of Bath | Storage Temp While Aging | % [Cl]* Bias | % Reduction Against Control |
| --- | --- | --- | --- | --- |
| Control | None-water only | 55° F. | −16.4 | — |
|  |  | 78° F. | −35.5 | — |
| 18 | Ca(NO$_3$)$_2$ (0.015 $\underline{M}$) | 42° F. | −1.0 | 93.9 |
|  |  | 70° F. | −5.7 | 83.9 |
| 19 | FeSO$_4$ (0.015 $\underline{M}$) | 42° F. | −8.0 | 51.2 |
|  |  | 70° F. | −11.1 | 68.7 |
| 20 | CdSO$_4$ (0.015 $\underline{M}$) | 42° F. | −0.3 | 98.2 |
|  |  | 70° F. | −1.5 | 95.8 |
| 21 | Ca(NO$_3$)$_2$ (0.424 $\underline{M}$) | 42° F. | −3.7 | 77.4 |
|  |  | 70° F. | −3.6 | 89.9 |
| Compar. Example 5 | Na Acetate (0.015 $\underline{M}$) | 42° F. | −25.1 | worse than control |
|  |  | 70° F. | −60.2 | worse than control |

*As defined in Example 16 and 17, Table III.

EXAMPLE 22

NaNO$_3$ Solution

The procedure of Example 18 was repeated, except the salt solution of the wash was 0.015M NaNO$_3$. The ISE was stored at 24° C. for two days, and at −13° C. for a short period, prior to testing. The results appear in Table V:

TABLE V

| Example | Salt Composition | Read Time After Spotting | % [Cl]* Bias | % Reduction Against Control |
|---|---|---|---|---|
| Control | None (Water only) | 3 Min | −9.87 | — |
| 22 | NaNO$_3$ | 3 Min | −0.57 | 94.2 |

*As explained in Table III.

The invention has been described in detail with particular reference to preferred embodiments thereof, but it will be understood that variations and modifications can be effected within the spirit and scope of the invention.

What is claimed is:

1. In a process for making an ion selective electrode selective for chloride, comprising the steps of
    (a) forming a layer of silver on a support, and
    (b) oxidizing a surface portion of the silver layer with a bath comprising a chlorochromate, to form silver chloride;
    the improvement comprising a further step, after step (b), of washing said electrode in an organic acid, inorganic acid, or aqueous solution of a salt of said organic or inorganic acid, provided that
    (a) said acid has a pKa <4.0 and a silver solubility product pK$_{sp}$ <10.0, in a concentration and for a length of time effective to reduce negative biases created by purine interferences when using an electrode prepared without said further step; and
    (b) said salt;
        (i) is soluble in water at ≧0.001M,
        (ii) yields an aqueous pH of ≦7.0, and
        (iii) comprises ions that do not dissolve said silver chloride, the cations being univalent or divalent cations only.

2. In a process for making an ion selective electrode selective for chloride, comprising the steps of
    (a) forming a layer of conductive metal on a support, and
    (b) oxidizing a surface portion of the metal layer with a bath comprising a chlorochromate to form MCl wherein M is the conductive metal,
    the improvement comprising a further step, after step (b), of washing said MCl layer in HNO$_3$ or H$_3$PO$_4$ having a concentration of from about 0.01M to about 1.0M, for a length of time of between about 5 min and about 0.5 min. respectively, such concentration and such length of time being effective to reduce negative purine biases created in the absence of the washing step 3. In a process for making an ion selective electrode selective for chloride, comprising the steps of
    (a) forming a layer of conductive metal on a support, and
    (b) oxidizing a surface portion of the metal layer with a bath comprising a chlorochromate to form MCl wherein M is conductive metal,
    the improvement comprising a further step, after step (b), of washing said MCl layer in a solution of NaNO$_3$, Ca(NO$_3$)$_2$, CdSO$_4$ or FeSO$_4$ at a concentration of at least 0.015M, for a length of time of between about 0.5 min and about 5 min.

4. A process as defined in claim 2 or 3, and further including, after said washing step, the step of forming a layer of cellulose ester on said layer of MCl.

5. A process as defined in claim 2 or 3, wherein said chlorochromate comprises potassium chlorochromate in a concentration of from about 0.002 to about 0.2M.

6. A process as defined in claim 2 or 3, and further including, after said washing step, the step of washing the metal chloride layer with water.

* * * * *